(12) United States Patent
Kiliç et al.

(10) Patent No.: US 12,121,467 B2
(45) Date of Patent: Oct. 22, 2024

(54) PAIR OF SUPPORTIVE SOCKS FOR DISORDERS CAUSED BY FOOT DEFORMITIES

(71) Applicant: ÖRMECI ÇORAP SANAYI VE TICARET LIMITED ŞIRKETI, Arnavutköy/Istanbul (AR)

(72) Inventors: Talha Kiliç, Arnavutköy/Istanbul (TR); Veli Akbal, Arnavutköy/Istanbul (TR)

(73) Assignee: ÖRMECI ÇORAP SANAYI VE TICARET LIMITED ŞIRKETI, Istanbul (TR)

( * ) Notice: Subject to any disclaimer, the term of this patent is extended or adjusted under 35 U.S.C. 154(b) by 617 days.

(21) Appl. No.: 17/293,549

(22) PCT Filed: May 16, 2019

(86) PCT No.: PCT/TR2019/000039
§ 371 (c)(1),
(2) Date: May 13, 2021

(87) PCT Pub. No.: WO2020/231352
PCT Pub. Date: Nov. 19, 2020

(65) Prior Publication Data
US 2022/0133515 A1   May 5, 2022

(51) Int. Cl.
*A61F 5/01* (2006.01)
*A41B 11/02* (2006.01)

(52) U.S. Cl.
CPC .............. *A61F 5/019* (2013.01); *A41B 11/02* (2013.01); *A61F 5/0111* (2013.01)

(58) Field of Classification Search
CPC ............ A61F 5/01–0104; A61F 5/0127; A61F 13/06; A61F 13/064–085; A61F 5/0111; A61F 5/0113; A61F 5/0195; A61F 5/0585; A61F 2013/0028; A61F 13/043; A61F 15/004; A61F 5/019; A61F 5/14; A61F 5/0118; A61F 13/068; A41B 11/00; A41D 13/05
See application file for complete search history.

(56) References Cited

U.S. PATENT DOCUMENTS

2006/0247566 A1* 11/2006 Gobet ................ A61F 13/08
602/62
2010/0088803 A1* 4/2010 Orloff ................ G09B 19/0038
434/258

FOREIGN PATENT DOCUMENTS

| DE | 202017106068 | | 11/2017 | |
|---|---|---|---|---|
| GR | 1009378 | | 10/2018 | |
| JP | 2007277779 | | 10/2007 | |
| JP | 4553269 | B1 | 9/2010 | |
| JP | 2012034718 | A | 2/2012 | |
| JP | 2018003217 | | 1/2018 | |
| TW | 1657811 | B * | 5/2019 | ........... A61F 5/0102 |

OTHER PUBLICATIONS

Int'l Search Report for PCT/TR2019/000039, issued Nov. 3, 2020.

* cited by examiner

*Primary Examiner* — Ophelia A Hawthorne
(74) *Attorney, Agent, or Firm* — MaxGoLaw PLLC

(57) ABSTRACT

A supporting pair of socks for disorders caused by foot deformities is provided that can be worn on a daily basis and allows comforting of the foot in case of flatfoot and hallux valgus disorder.

8 Claims, 2 Drawing Sheets

PAIR OF SUPPORTIVE SOCKS FOR DISORDERS CAUSED BY FOOT DEFORMITIES

TECHNICAL FIELD

Figure 1:
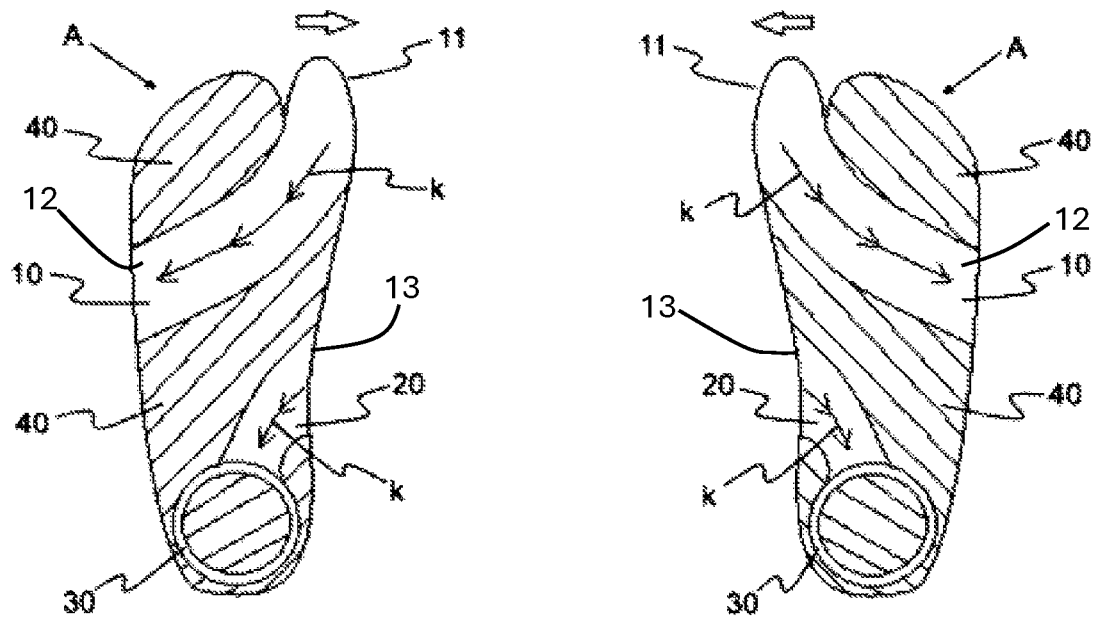

The invention is about a pair of supportive socks for problems related with foot deformities.

In particular, the invention is about a supportive pair of socks that can be worn on daily basis to support foot arch and muscles of persons who stand for a long time during daily activities and comfort foot in case of disorders particularly including flatfoot and hallux valgus.

State of the Art

The disease defined as big toe bump and known as hallux valgus in the field of medicine is a foot deformation that is diagnosed with permanent deformation of the big toe to the side, formation of a painful bone bump in the inner side of the foot where big toe creates a joint with metacarpus and expansion of the foot on the metacarpus zone. It makes walking difficult due to pain and expansion of the foot and bone bump leads to adverse effects on daily life by making wearing footwear difficult.

Flatfoot is a foot deformation that is characterized with deformation of the heel towards the outer side upon disappearance of the inner cavity that should be present under normal conditions. In case of flatfoot disorder, there is pain in the inner side of the foot and therefore, patients step towards the inner side.

In the existing technique, arch support and certain big toe stabilizers are used in connection with disorders related with foot deformations explained above. These are usually medical products that are especially produced for patients with flatfoot or hallux valgus. Therefore, it is impossible to eliminate both disorders by using a single product. In addition, they lead to loss of comfort because of problems created on the skin and thus, they cannot be used in any condition and lead to problems about adaptation of the patient. Such products are costly products and they are not aesthetic, and they are very visible. In addition, they are easily accessible medical products that require special measurements for the patients. Further, one of the disadvantages of these products is the fact that they are chemically treated.

In the literature, one of the relevant documents is the document no. JP2007330743. This document is about a support that has an adjustment belt. This support is in the form of a belt that is inserted to the end of foot by grabbing the big toe and small toe and it is wrapped around sides of the foot and adjusted from the ankle.

Another example of the state of the art is the document no. JP2018118012. This document is related with a support that is attached to foot for the purpose of preventing or correcting hallux valgus. The support is made of a flexible fabric an consists of a big toe part that is used to place a foot attachment part in order to insert to the big toe.

Both inventions mentioned above are intended for using in connection with hallux valgus and a pressure force is applied on lateral plane of the foot end. Therefore, their structure is not suitable for preventing flatfoot disorder and the use of these products in footwear is difficult and disturbing during daily activities.

In conclusion, the presence of the problems described above, and inadequacy of existing solutions made it compulsory to make a development in the relevant technical field.

Objective of Invention

The present invention is related with a supportive pair of socks for disorders related with foot deformation that brings new advantages to the relevant technical field and eliminates the disadvantages explained above.

Main objective of the invention is to ensure that foot is comforted by applying strength to keep feet in normal position in case of flatfoot and hallux valgus disorders and also to support foot arch and muscles of persons who stand for a long time during daily activities.

Another objective of the invention is that it is a supportive pair of socks that can be worn on daily basis and it affects flatfoot and hallux valgus disorders in a comforting way.

Another objective of the invention is to create comforting effect on both legs and waist due to the support given to feet.

Another objective of the invention is to provide comfort and sense of relaxation to feet.

Another objective of the invention is the ease of supply, access and use as special measurement is not required and it is produced in accordance with foot size.

Another objective of the invention is to wear anywhere, whether in and out of footwear, in all seasons including winter and summer and to ensure full adaptation to daily life of the individual.

Another objective of the invention is cost-efficiency compared to apparatus used for flatfoot and hallux valgus disorders and it is hygienic due to possibility of washing.

Another objective of the invention is to provide strength towards normalization of foot dynamics, different from normal socks due to its special weaving modelling.

Another objective of the invention is the fact that the only difference distinguishing from normal pair of socks is the separation of big toe from other four toes in terms of aesthetics.

For the purpose of achieving all objectives that are explained above and can be retrieved from the detailed description, the invention is about a supportive pair of socks for disorders related with foot disorders. The invention features:

weaving for the big toe that separates big toe from other toes and the first strength zone that continues to the upper side of the foot in a spiral direction in order to transfer the strength from the sole to the cavity in the inner side of foot; pull the elevation of the foot to the upper direction and create an elliptic zone with higher strength from the side of the foot where big toe creates a joint with the foot;

the second strength zone that balances the strength by increasing the inner elevation; extends towards outer sides of the foot by creating a curve towards the ankle and then, extends from the peak point of the cavity in the inner side of the cavity;

ankle grabbing zone that continues over the bone bumps in the ankle and wrapping both bones on ankle in the form of a circle as a balancing force for the strength in the force direction and force line created in the said first strength zone and second strength zone;

weave with lower strength in the areas other than the said first strength zone, second strength zone and ankle wrapping zone.

Structure of the invention and its characteristic properties and all advantages will be clearly understood in reference to figures provided below and detailed explanations provided

FIGURES INTENDED TO ASSIST EXPLANATION OF THE INVENTION

FIG. 1: Top view of socks constituting subject matter of invention when worn on the left foot and right foot FIG. 2: Bottom view of socks constituting subject matter of invention when worn on the left foot and right foot FIG. 3: Side view of socks constituting subject matter of invention when worn on the right foot FIG. 4: Side view of socks constituting subject matter of invention when worn on the left foot.

REFERENCE DESCRIPTION OF PARTS

A. Sock
10. First strength zone
11. Big toe weaving
20. Second strength zone
30. Ankle wrapping zone
40. Weaving with lower strength
k. Force direction and force line

DETAILED DESCRIPTION OF INVENTION

In this description, preferred alternative of the pair of socks (A) constituting subject matter of the invention is described without any limiting effect and for the purpose of better understanding of the concept.

Figure 2:
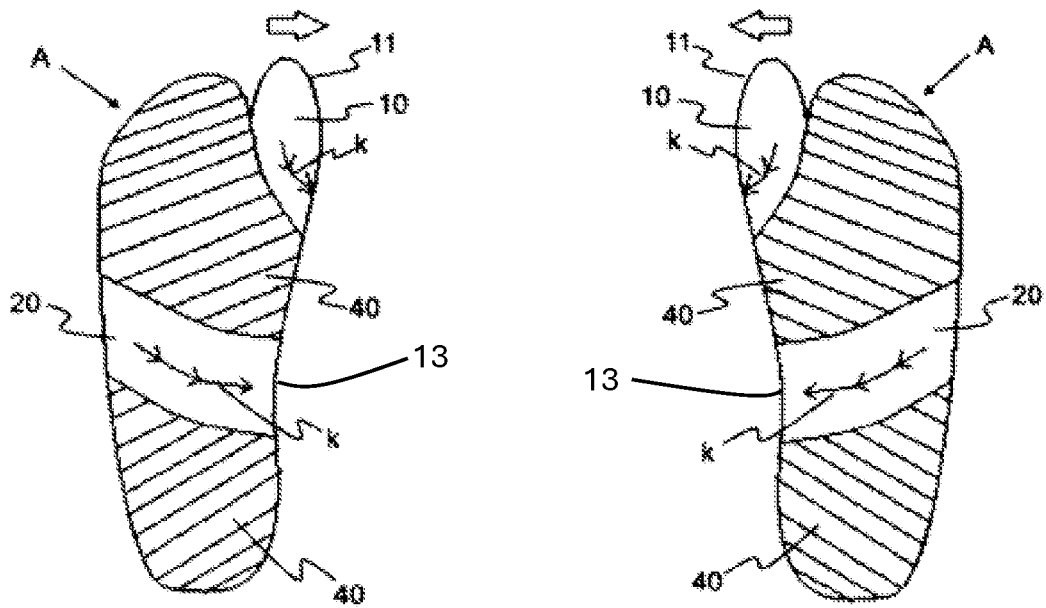

FIGS. 1 and 2 provides top and bottom views of the pair of socks (A) constituting subject matter of invention. Accordingly, in its most basic form, the pair of socks (A) consists of the first strength zone (10) that is in a spiral direction and pulls the strength from the sole to the curve (12) in the inner side of the foot in order to pull the elevation of the foot in an upper direction; second strength zone (20) that creates a curve (12) towards the ankle in order to balance the strength by increasing the inner elevation of the foot; ankle wrapping area (30) that continues over the bone bumps on the ankle for the purpose of balancing the strength; and weaving with a lower strength (40) that is created by zones other than the first strength zone (10), second strength zone (20) and ankle wrapping area (30).

Any type of yarn can be used for weaving the pair of socks (A) constituting subject matter of the invention. Weaving methods creates the strength. This pair of socks can be applied to any model including socket socks, socks to the knee level, socks above the knee level, socks to the hip level, pantyhose and any other type of model.

As FIGS. 1 and 2 show, the first strength zone (10) separates big toe from other toes. Big toe weaving (11) is woven separate from the other four toes and it is performed with weaving method that creates high strength.

Figure 3:
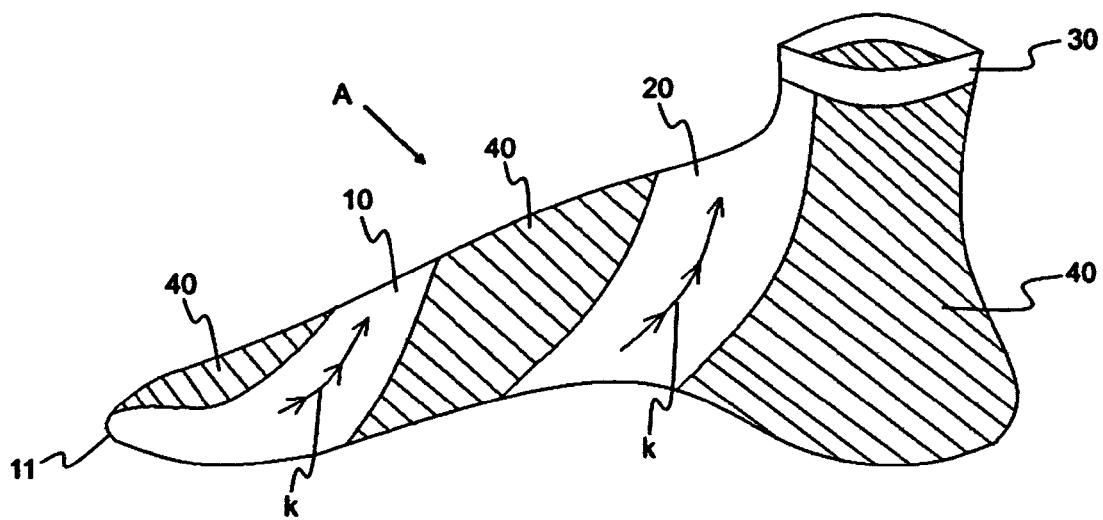
Figure 4:
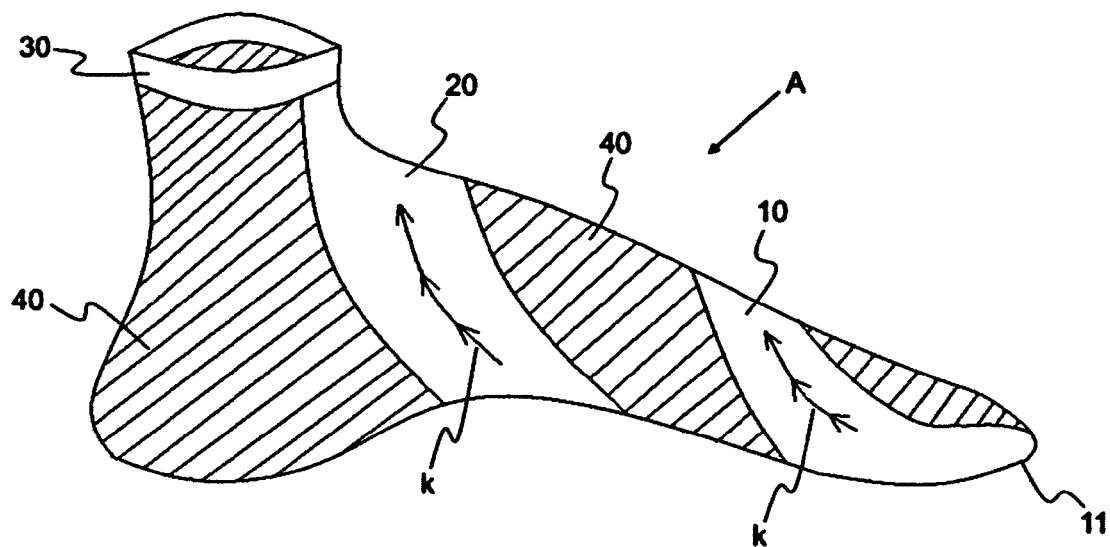

As FIGS. 3 and 4 show, the first strength zone (10) extends in spiral direction from inner side of the foot where big toe forms a joint with the foot to the upper part of the foot in an elliptical manner and such that strength is higher in order to pull elevation of the foot to the upper direction by transferring the strength from sole of the foot to the curve in the inner side.

The second strength zone (20), extends from the middle portion of the outer side of the foot, creating a curve towards the ankle and balancing the strength by increasing the inner elevation of the foot. Then, it extends from the peak point (13) of the curve in the inner side of the foot, The ankle wrapping area (30) wraps two bones on the ankle in a circular shape by extending over the bone bumps on the ankle in order to balance the strength in the force direction and force line (k) created in the first strength zone (10) and the second strength zone (20). Thus, the tension force taken from the big toe is transferred from the outer side of the foot in order to apply pressure to the inner peak point (13), thus lifting the inner peak point (13) upwards and separating the big toe from the other toes to the inner side. Ankle wrapping zone (30) uses bone bumps on ankles as stabilizing points in order to balance this interaction of forces and allows fixation on the ankle.

Zones other than the first strength zone (10), second strength zone (20) and ankle wrapping zone (30) feature weaving with lower strength (40).

The invention claimed is:

1. A supporting sock for disorders related with foot deformation comprising:
a first strength zone that features a big toe weaving, the big toe weaving partially separated from a portion of the supporting sock that is configured to receive a plurality of other toes of a foot, the big toe weaving configured to receive only a big toe of the foot and to pull the big toe toward an inner side of the foot away from the plurality of other toes, the big toe weaving configured to extend from the inner side of the foot where the big toe creates a joint with the foot in an elliptical manner and to continue in a spiral direction towards an upper side of the foot with a strength that increases in order to transfer the strength from a sole to a curve in the inner side of the foot, the first strength zone configured to provide a first force direction and a first force line that extends diagonally over a top of the foot from the big toe to an outer side of the foot;
a second strength zone configured to provide a second force direction and a second force line, the second strength zone is configured to extend from a middle outer part of the foot and curve towards an ankle to a peak point of the curve located in an arch of the inner side of the foot and then, continuing from the peak point of the curve towards the ankle in order to balance the strength by increasing an inner elevation of the arch of the inner side of the foot;
an ankle wrapping zone that is configured to wrap two bones on the ankle in a circular shape by extending over bone bumps on the ankle for balancing the strength on a force direction and force line created in the first strength zone and the second strength zone; and
a weaving with a lower strength created by a plurality of zones other than the first strength zone, the second strength zone and the ankle wrapping zone; and
wherein the first force line and the second force line are configured to be parallel to each other on the inner side of the foot.

2. The supporting sock consistent with claim 1 wherein the first strength zone, the second strength zone, the ankle wrapping zone, and the weaving are all formed from a yarn.

3. The supporting sock consistent with claim 1 wherein a weaving method creates a plurality of different strengths of the first strength zone, the second strength zone, the ankle wrapping zone, and the weaving.

4. The supporting sock consistent with claim 1 wherein the big toe weaving has a high-strength weaving that is configured to separate the big toe from the plurality of other toes.

5. The supporting sock consistent with claim 1 wherein the ankle wrapping zone extends to a height of a socket sock.

6. The supporting sock consistent with claim 1 wherein the ankle wrapping zone extends to a height of a knee level sock.

7. The supporting sock consistent with claim 1 wherein the ankle wrapping zone extends to a height of a hip level sock.

8. The supporting sock consistent with claim 1 wherein the ankle wrapping zone extends to a height of a pantyhose.

\* \* \* \* \*